US012765550B2

(12) United States Patent
Lindner et al.

(10) Patent No.: US 12,765,550 B2
(45) Date of Patent: Oct. 20, 2026

(54) AGROCHEMICAL ADJUVANTS

(71) Applicants: Croda International Plc, Goole (GB); Croda, Inc., Plainsboro, NJ (US)

(72) Inventors: Gregory James Lindner, Plainsboro, NJ (US); Bradley Arnold Haltli, Charlottetown (CA); Russell Greig Kerr, Charlottetown (CA); Alyssa Louise Grunwald, Charlottetown (CA); Hebelin Correa Velandia, Charlottetown (CA)

(73) Assignees: Croda International Plc, Goole (GB); Croda, Inc., Plainsboro, NJ (US)

( * ) Notice: Subject to any disclaimer, the term of this patent is extended or adjusted under 35 U.S.C. 154(b) by 812 days.

(21) Appl. No.: 17/916,346

(22) PCT Filed: Apr. 2, 2021

(86) PCT No.: PCT/US2021/025498

§ 371 (c)(1),
(2) Date: Sep. 30, 2022

(87) PCT Pub. No.: WO2021/202951

PCT Pub. Date: Oct. 7, 2021

(65) Prior Publication Data

US 2023/0120044 A1 Apr. 20, 2023

Related U.S. Application Data

(60) Provisional application No. 63/004,875, filed on Apr. 3, 2020.

(51) Int. Cl.

*A01N 43/16* (2006.01)
*A01P 3/00* (2006.01)
*C12N 1/14* (2026.01)

(52) U.S. Cl.

CPC ................ *A01N 43/16* (2013.01); *A01P 3/00* (2021.08); *C12N 1/14* (2013.01)

(58) Field of Classification Search

None

See application file for complete search history.

(56) References Cited

FOREIGN PATENT DOCUMENTS

| | | | |
|---|---|---|---|
| CN | 101263810 | A | 9/2008 |
| WO | 9400508 | A1 | 1/1994 |
| WO | 9616930 | A1 | 6/1996 |
| WO | 2017075527 | A1 | 5/2017 |

OTHER PUBLICATIONS

McCorkindale, N. J. et al. "Lamellicolic Anhydride . . ." J. C. S. Chem. Comm., 1973, 108-109.*

McRitchie (https://theses.gla.ac.uk/78634/1/11017941.pdf, 1973 doctoral thesis "Lamellicolic Anhydride and other polyketides . . ."), 1973, entire document p. 1-139 and unnumbered pages.*

McCorkindale et al. (J. of the Chem. Soc., Chem. Comm., 1973, 108-109).*

Elsebai et al., "Antimicrobial phenalenone derivatives from the marine-derived fungus Coniothyrium cereale", Org. Biomol. Chem., 2011, 9, pp. 802-808.

Grafenhan et al., "An overview of the taxonomy, phylogeny, and typification of nectriaceous fungi in Cosmospora, Acremonium, Fusarium, Stilbella, and Volutella", Studies in Microbiology, 2011, 68, pp. 79-113.

International Search Report and Written Opinion for International Application No. PCT/US2021/025498, dated Aug. 11, 2021, 13 pages.

Matsumoto et al., "Structure in Ilicicolin H, an Antifungal Antibiotic", Tetrahedron Letters, 1976, No. 42, pp. 3827-3830.

McCorkindale et al., "Lamellicolic Anhydride, 4-O-Carbomethoxylamellicolic Anhydride and Monomethyl 3-Chlorolamellicolate, Metabolites of Verticillium Lamellicola", Tetrahedron, 1983, vol. 39, No. 13, pp. 2283-2288.

Singh et al., "Antifungal Spectrum, In Vivo Efficacy, and Structure-Activity Relationship of Ilicicolin H", ACS Med. Chem. Lett., 2012, 3, pp. 814-817.

Office Action (Notice of Reasons for Refusal) issued Mar. 4, 2025, by the Japanese Patent Office in corresponding Japanese Patent Application No. 2022-560017 and an English translation of the Office Action. (9 pages).

International Preliminary Report on Patentability and Written Opinion for International Application No. PCT/US2021/025498, issued Sep. 29, 2022, 9 pages.

Office Action (Communication pursuant to Article 94(3) (EPC) issued Oct. 24, 2025, by the European Patent Office in corresponding European Patent Application No. 21 720 925.3-1102. (5 pages).

* cited by examiner

*Primary Examiner* — Erin E Hirt

(74) *Attorney, Agent, or Firm* — Buchanan Ingersoll & Rooney PC

(57) ABSTRACT

A novel agrochemical formulation comprising adjuvants selected from ilicicolins and lamellicolic anhydrides and an agrochemical active is described. A concentrate is also provided suitable for forming the formulation. The ilicicolins and lamellicolic anhydrides provide adjuvancy in the concentrate and agrochemical formulation. Use of said ilicicolins and lamellicolic anhydrides as adjuvants in agrochemical formulations is also provided. There is also provided a method of making the formulation, and for treating soil with the formulations. A method of obtaining the ilicicolins and lamellicolic anhydrides from culturing of *Cosmospora* sp., strain RKD01747 is also described.

12 Claims, No Drawings

AGROCHEMICAL ADJUVANTS

CROSS-REFERENCE TO RELATED APPLICATIONS

This is the U.S. National Phase application of PCT/US2021/025498, filed Apr. 2, 2021, which claims priority to U.S. Provisional Application No. 63/004,875, entitled "AGROCHEMICAL ADJUVANTS", filed Apr. 3, 2020, the content of each of which is incorporated herein by reference in its entirety for all purposes.

FIELD OF THE INVENTION

The invention relates generally to adjuvants obtainable from microbials for agrochemical active formulations, and a method of providing adjuvancy in agrochemical formulations comprising said adjuvants with one or more agrochemical actives. The present invention also includes treating crops with said formulations.

BACKGROUND OF THE INVENTION

An adjuvant is generally defined as a chemical or a mixture of chemicals capable of improving the biological activity or effectiveness of an agrochemical active. Adjuvants do not themselves control or kill pests. Instead, these additives may interact with molecular targets (e.g. cell wall, ion channels, structural proteins, enzymes, etc.) within the target organism, or modify some property (e.g. spreading, retention, penetration, droplet size) of the agrochemical formulation, thereby improving the biological activity of the agrochemical active on the organism. The typical types of compounds used as adjuvants may include small molecules, surfactants, emulsifiers, oils, and salts. Adjuvants do not typically inhibit translocation of the active in the treated plant. In addition, the adjuvant should not produce unwanted phytotoxic effects on the plant.

Fungi are widespread in terrestrial environments and present a major challenge to agricultural productivity. Unchecked fungal infections can result in pre- and post-harvest crop losses that can exceed 80%. In order to help reduce such losses and meet increasing food needs, the use of fungicides to control fungal agricultural pests is, and will continue to be, an important component of agricultural pest management systems.

There is a need to develop new strategies to combat agricultural pests, especially fungal pests. One strategy is to develop adjuvants that are safe, non-toxic chemicals which improve the effectiveness of existing fungicides already approved for use on field and greenhouse crops to prevent or reduce the impact of fungal pests on agricultural productivity. These adjuvants can improve the control of pests in the field or after harvest, thereby increasing productivity. They may also reduce the quantities of fungicide required to achieve the desired level of pest control, thus contributing to the goal of achieving sustainable productivity increases.

The present invention seeks to provide the use of compounds in agrochemical formulations in combination with an agrochemical active, where the compounds may provide desired adjuvancy, including improved efficacy of the active. The present invention also seeks to provide the use of agrochemical concentrates and dilute formulations comprising said adjuvants.

The present invention also seeks to provide compounds in agrochemical formulations, where the compounds may provide comparable or improved adjuvancy properties compared to existing adjuvants.

The present invention also seeks to provide the use of compounds as adjuvants, and formulations comprising said compounds for use in providing adjuvancy in agrochemical formulations.

SUMMARY OF THE INVENTION

According to a first aspect of the present invention there is provided an agrochemical formulation comprising;

i) an adjuvant selected from ilicicolin H, hydroxy ilicicolin H, ilicicolin I, or a lamellicolic anhydride according to formula (I)

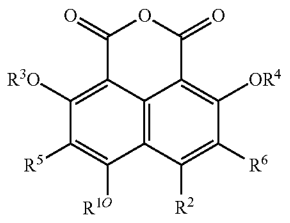

wherein:

$R^1$ independently represents hydrogen or $C_1$ to $C_4$ alkyl;

$R^2$ independently represents hydrogen, $C_1$ to $C_4$ alkyl, hydroxyl, or $C_1$ to $C_4$ alkyoxyl;

$R^3$ and $R^4$ independently represents hydrogen or $C_1$ to $C_4$ alkyl; and $R^5$ and $R^6$ independently represents hydrogen, $C_1$ to $C_4$ alkyl, hydroxyl, or $C_1$ to $C_4$ alkyoxyl; and ii) at least one agrochemical active.

According to a second aspect of the present invention there is provided a concentrate formulation suitable for making an agrochemical formulation of the first aspect, said concentrate comprising;

i) an adjuvant selected from ilicicolin H, hydroxy ilicicolin H, ilicicolin I, or a lamellicolic anhydride according to formula (I)

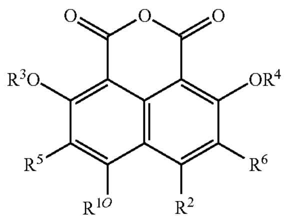

wherein:

$R^1$ independently represents hydrogen or $C_1$ to $C_4$ alkyl;

$R^2$ independently represents hydrogen, $C_1$ to $C_4$ alkyl, hydroxyl, or $C_1$ to $C_4$ alkyoxyl;

$R^3$ and $R^4$ independently represents hydrogen or $C_1$ to $C_4$ alkyl; and $R^5$ and $R^6$ independently represents hydrogen, $C_1$ to $C_4$ alkyl, hydroxyl, or $C_1$ to $C_4$ alkyoxyl; and ii) at least one agrochemical active.

According to a third aspect of the present invention there is provided the use of a compound selected from ilicicolin H, hydroxy ilicicolin H, ilicicolin I, or a lamellicolic anhydride according to formula (I)

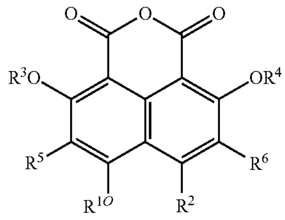

wherein:

$R^1$ independently represents hydrogen or $C_1$ to $C_4$ alkyl;

$R^2$ independently represents hydrogen, $C_1$ to $C_4$ alkyl, hydroxyl, or $C_1$ to $C_4$ alkyoxyl;

$R^3$ and $R^4$ independently represents hydrogen or $C_1$ to $C_4$ alkyl; and $R^5$ and $R^6$ independently represents hydrogen, $C_1$ to $C_4$ alkyl, hydroxyl, or $C_1$ to $C_4$ alkyoxyl;

as an adjuvant in an agrochemical formulation comprising at least one agrochemical active.

According to a fourth aspect of the present invention there is provided a method of treating vegetation to control pests, the method comprising applying a formulation of the first aspect, or a diluted concentrate formulation of the second aspect, either to said vegetation or to the immediate environment of said vegetation.

According to a fifth aspect of the present invention there is provided a method of obtaining adjuvants according to the first aspect comprising the steps of:

culturing *Cosmospora* sp. RKDO1747 in a medium under conditions which promote the metabolic synthesis of a fungicide adjuvant according to the first aspect from the *Cosmospora* sp. and purifying the synthesised adjuvant from the cultured medium.

According to a sixth aspect of the present invention there is provided an organism consisting of *Cosmospora* sp., strain RKDO1747, Agricultural Research Service Culture Collection (NRRL) accession number NRRL-67910.

According to a seventh aspect of the present invention there is provided an extract obtained from the organism consisting of *Cosmospora* sp., strain RKDO1747, Agricultural Research Service Culture Collection (NRRL) accession number NRRL-67910, said extract comprising at least one of ilicicolin H, hydroxy ilicicolin H, ilicicolin I, or lamellicolic anhydride in accordance with the first aspect.

According to an eighth aspect of the present invention there is provided a method of treating vegetation to control pests, the method comprising applying an organism of the sixth aspect either to said vegetation or to the immediate environment of said vegetation.

According to a ninth aspect of the present invention there is provided a seed coating composition comprising adjuvants according to the first aspect or organisms according to the sixth aspect.

According to a tenth aspect of the present invention there is provided a lamellicolic anhydride according to formula (I)

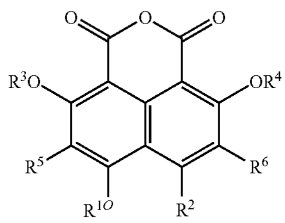

wherein:

$R^1$, $R^3$, $R^4$, and $R^6$ are all hydrogen, $R^5$ is hydroxyl, and $R^2$ is methyl; or $R^1$, $R^4$, $R^5$, and $R^6$ are all hydrogen, and $R^2$ and $R^3$ are methyl; or $R^4$, $R^5$, and $R^6$ are all hydrogen, and $R^2$, $R^3$ and $R^1$ are methyl; or $R^3$, $R^5$, and $R^6$ are all hydrogen, and $R^2$, $R^4$ and $R^1$ are methyl; or $R^4$ and $R^5$ are hydrogen, $R^2$, $R^3$ and $R^1$ are methyl, and $R^6$ is hydroxyl; or $R^3$ and $R^5$ are hydrogen, $R^2$, $R^4$ and $R^1$ are methyl, and $R^6$ is hydroxyl.

DETAILED DESCRIPTION OF THE INVENTION

It has been found that the compounds as defined herein provide for desired adjuvancy properties when used in an agrochemical formulation having at least one agrochemical active. Importantly, the compounds of the class identified, lamellicolic anhydrides and ilicicolins, do not show intrinsic pesticidal activity.

As used herein, the terms 'for example,' 'for instance,' 'such as,' or 'including' are meant to introduce examples that further clarify more general subject matter. Unless otherwise specified, these examples are provided only as an aid for understanding the applications illustrated in the present disclosure, and are not meant to be limiting in any fashion.

It will be understood that, when describing the number of carbon atoms in a substituent group (e.g. '$C_1$ to $C_4$ alkyl'), the number refers to the total number of carbon atoms present in the substituent group, including any present in any branched groups. Additionally, when describing the number of carbon atoms in, for example fatty acids, this refers to the total number of carbon atoms including the one at the carboxylic acid, and any present in any branched groups.

The ilicicolin compounds are selected from ilicicolin H, hydroxy ilicicolin H, or ilicicolin I. Preferably, the ilicicolin compound is ilicicolin H.

The ilicicolin compounds will be understood to be adjuvants, and will be referred to as such throughout.

The structure of ilicicolin H is 5-(4-hydroxyphenyl)-2-pyridone with a bicyclic decalin system. It will be understood that the ilicicolin H compound refers to a compound having a structure of formula (A);

(A)

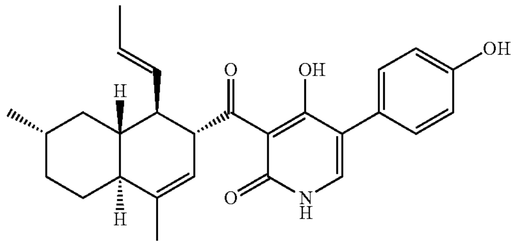

The structure of hydroxy-ilicicolin H is identical to ilicicolin H with a further hydroxyl group. It will be understood that the hydroxy-ilicicolin H compound refers to a compound having a structure of formula (B);

(B)

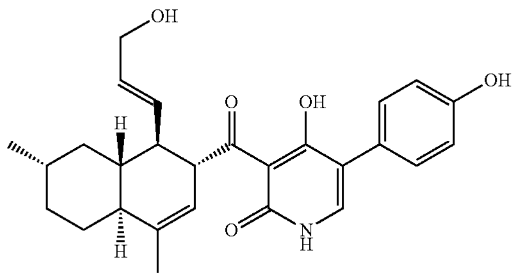

The structure of ilicicolin I is a further variation on the bicyclic decalin system. It will be understood that the ilicicolin I compound refers to a compound having a structure of formula (C);

(C)

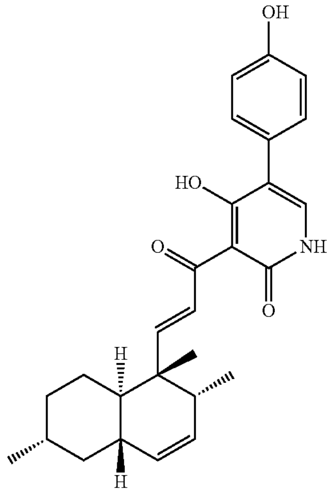

The adjuvants of the present invention may also be selected from lamellicolic anhydrides. It will be understood that the adjuvants are preferably selected from lamellicolic anhydrides.

The lamellicolic anhydrides are selected from those having a structure of formula (I):

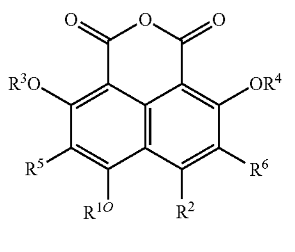

wherein:

$R^1$ independently represents hydrogen or $C_1$ to $C_4$ alkyl;

$R^2$ independently represents hydrogen, $C_1$ to $C_4$ alkyl, hydroxyl, or $C_1$ to $C_4$ alkyoxyl;

$R^3$ and $R^4$ independently represents hydrogen or $C_1$ to $C_4$ alkyl; and $R^5$ and $R^6$ independently represents hydrogen, $C_1$ to $C_4$ alkyl, hydroxyl, or $C_1$ to $C_4$ alkyoxyl.

The term '$C_1$ to $C_4$ alkyl' as used herein, unless otherwise defined, refers to saturated hydrocarbon radicals being straight chain or branched, containing from 1 to 4 carbon atoms. Where any of $R^1$ to $R^6$ represent $C_1$ to $C_4$ alkyl, said alkyl may be independently selected from methyl, ethyl, n-propyl, isopropyl, n-butyl, isobutyl, sec-butyl, tert-butyl, or the like. Preferably, the $C_1$ to $C_4$ alkyl is methyl or ethyl. More preferably, the $C_1$ to $C_4$ alkyl is methyl.

The term '$C_1$ to $C_4$ alkoxyl' as used herein, unless otherwise defined, refers to alkyl groups linked to oxygen which form an alkoxy radical having the structure —O-Alk, and which are bonded to an adjacent radical via the oxygen, where Alk represents a $C_1$ to $C_4$ alkyl group as defined herein.

Where any of $R^2$, $R^5$, and $R^6$ represent $C_1$ to $C_4$ alkyoxyl, said alkyoxyl may be independently selected from methoxy, ethoxy, butoxy, propanoxy, or the like. Preferably, the $C_1$ to $C_4$ alkyoxyl is methoxy or ethoxy. More preferably, the $C_1$ to $C_4$ alkyoxyl is methoxy.

Preferably, compounds of formula (I) are selected from those where:

$R^1$ independently represents hydrogen or methyl;

$R^2$ independently represents hydrogen or methyl, preferably methyl;

$R^3$ and $R^4$ independently represents hydrogen or methyl, preferably both hydrogen or one being hydrogen and the other methyl; and $R^5$ and $R^6$ independently represents hydrogen or hydroxyl, preferably both hydrogen or one being hydrogen and the other hydroxyl.

More preferably, compounds of formula (I) are selected from those where:

$R_1$, $R^3$, $R^4$, $R^5$, and $R^6$ are all hydrogen, and $R^2$ is methyl; or $R_1$, $R^3$, $R^4$, and $R^6$ are all hydrogen, $R^5$ is hydroxyl, and $R^2$ is methyl; or $R_1$, $R^4$, $R^5$, and $R^6$ are all hydrogen, and $R^2$ and $R^3$ are methyl; or $R^4$, $R^5$, and $R^6$ are all hydrogen, and $R^2$, $R^3$ and $R^1$ are methyl; or $R^3$, $R^5$, and $R^6$ are all hydrogen, and $R^2$, $R^4$ and $R^1$ are methyl; or $R^4$ and $R^5$ are hydrogen, $R^2$, $R^3$ and $R^1$ are methyl, and $R^6$ is hydroxyl; or $R^3$ and $R^5$ are hydrogen, $R^2$, $R^4$ and $R^1$ are methyl, and $R^6$ is hydroxyl.

In particular, lamellicolic anhydrides selected from the following may be preferred:

(Ia)

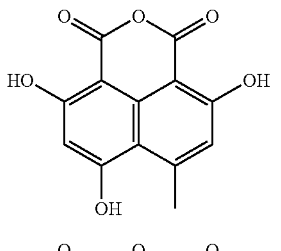

(Ib)

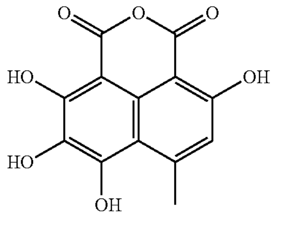

-continued (Ic)

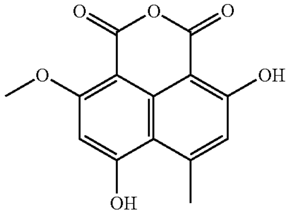

(Id)

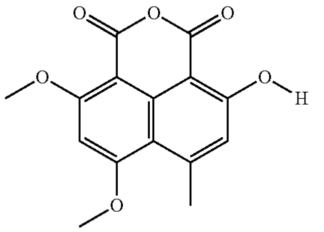

(Ie)

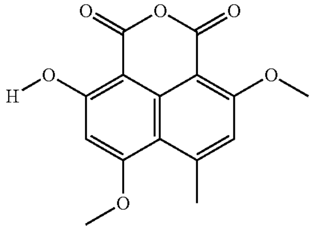

(If)

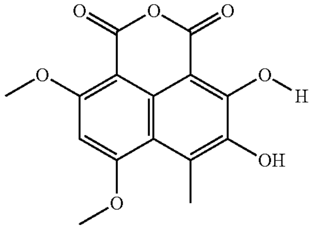

(Ig)

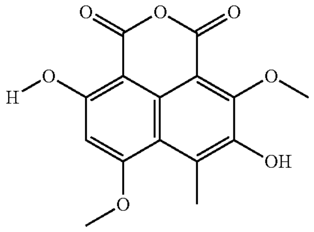

The organism employed in the fermentation is a filamentous fungus belonging to the genus *Cosmospora*. It has been found that certain strains of *Cosmospora* sp. RKDO1747 are especially useful in producing the novel adjuvant, and this strain has been made the subject of a deposit, under the Budapest Treaty, at the Agricultural Research Service Culture Collection (NRRL), Peoria, Illinois, USA:

| Species | Strain | Accession No. | Date of Deposit |
|---|---|---|---|
| *Cosmospora* sp. | RKDO1747 | 67910 | Jan. 10, 2020 |

NRRL-67910 is especially preferred in providing the fungicide adjuvant activities of the present invention.

The ilicicolins, or lamellicolic anhydrides can each be formed and extracted from cultures of a *Cosmospora* sp., and specifically RKDO1747. The desired compound can be extracted and purified from the culture liquid or the fungal biomass by any means typically used for generally collecting microbial metabolites. Examples include chromatography with adsorbent such as various ion exchange resins, non-ionic adsorbing resins, gel filtration chromatography, activated charcoal, alumina and silica gel, or a separation method by using high performance liquid chromatography, or crystallisation, concentration under reduced pressure, or lyophilisation, which means can be used alone or in appropriate combination thereof, or repeatedly.

The cultures of *Cosmospora* sp. RKDO1747, can be obtained from natural sources or from culture collections such as the Agricultural Research Service Culture Collection (NRRL). Isolates of *Cosmospora* sp. RKDO1747 can be cultured by methods known in the art of mycology.

As a means of producing the compounds of the present invention, the producing organism can be grown on any suitable synthetic mediums or natural mediums so long as they appropriately contain carbon sources, nitrogen sources, and inorganic salts. If necessary, mediums may be suitably supplemented with vitamins and other nutrient substances.

Examples of general carbon sources include (but are not limited to), sugars such as glucose, maltose, fructose, sucrose, and starch, alcohols such as glycerol, and mannitol, amino acids such as glycine, alanine, and asparagine, and oils and fats such as soy bean oil and olive oil. Examples of the nitrogen source include organic nitrogen-containing compounds such as soy bean powder, corn steep liquor, beef extract, peptone, yeast extract, amino acid mixtures, and fish powder, and inorganic nitrogen compounds such as ammonium salts and nitrates. As well, micro-nutrients in the form of inorganic salts can be used, for example, calcium carbonate, sodium chloride, potassium chloride, magnesium sulphate, copper sulphate, manganese chloride, zinc sulphate, cobalt chloride, and various phosphates.

The organism can be grown in an appropriate cultivation temperature within a range that allows growth of a microorganism and effective production of the compounds of the present invention. Preferred cultivation temperature is from 10° C. to 32° C., and more preferably from 20° C. to 25° C. The pH at the beginning of the cultivation is preferably from about 4 to 6. The cultivation period of time is generally about one day to a few weeks.

The cultivation may be terminated when a produced amount of the compound of the present invention reaches an amount suitable for collection, preferably when it reaches the maximum amount. As a cultivation method, any method can be suitably employed so far that the method is ordinarily used, such as solid state cultivation and normal stirring cultivation.

For example, isolates of *Cosmospora* sp. RKDO1747 can be plated onto nutrient-containing (e.g. YM (Yeast Malt extract)) agar, and incubated for several days at room temperature until observable colonies appear. Individual *Cosmospora* sp. RKDO1747 colonies on the agar can be assayed for production of ilicicolins or lamellicolic anhydrides.

Those colonies producing the desired molecules can be used to inoculate a broth culture (e.g. a YM broth culture), which can be cultured under suitable conditions (e.g. at room temperature with shaking for several days) to yield a seed inoculum. The seed inoculum can be used to initiate larger liquid cultures (e.g. potato dextrose broth) which can be incubated for several days (e.g. 4-28 days) at about room temperature to expand the *Cosmospora* sp. culture.

The ilicicolins and lamellicolic anhydrides are found to be excreted into the liquid medium (e.g. potato dextrose broth).

The ilicicolins and lamellicolic anhydrides can be isolated from fermentation broths using liquid:liquid extraction involving ethyl acetate and water as well as binding the compound to an absorptive resin (such as Diaion™ HP20), washing the resin with water and then eluting the lamellicolic anhydrides and ilicicolins using an appropriate solvent (such as methanol or ethanol). Due to differences in polarity of the ilicicolins and lamellicolic anhydrides, the individual compounds can be easily separated using chromatography, such as flash chromatography, and a reverse-phase stationary phase (such as C-18).

The resulting extracted ilicicolins and lamellicolic anhydrides may be purified and used as individual homogenous compounds. In an alternative embodiment, the extracted material may be a combination of the ilicicolins and lamellicolic anhydrides according to the first aspect, and may be used in combination in the agrochemical formulation.

In other embodiments, the ilicicolins and lamellicolic anhydrides might be obtained from other available resources, typically other fungi.

The ilicicolins or lamellicolic anhydrides might also be made by synthetic techniques. The lamellicolic anhydrides and its derivatives may be produced through chemical synthesis by one skilled in the art of organic chemistry using commercially available materials and synthetic methodology described in the scientific literature. Commercially available substances that are structurally related to the lamellicolic anhydrides and could be used as starting materials include, for instance but not limited to, 1,8-naphthalenedicarboxylic acid, 1,8-naphthalic anhydride, acenaphthene, and 5-bromoacenaphthene. Using naphthalene-based starting materials, the carboxylic acid functionalities can be protected using standard protecting group chemistry as required before completing aromatic functionalisation reactions.

The aryl methyl group of the lamellicolic anhydrides could be introduced by an electrophilic aromatic substitution, such as a Friedel-Crafts alkylation. Phenol groups could subsequently be introduced by electrophilic aromatic halogenations using, for instance, chlorine or bromine followed by nucleophilic aromatic substitution using sodium hydroxide. To introduce aryl methoxy groups, such as those found in lamellicolic anhydrides Ib and Ic, nucleophilic aromatic substitution using sodium methoxide may be performed. Protection and deprotection of the hydroxyl and carboxylic acid functionalities can be completed as required to allow for the generation of the anhydride moiety, which can occur by, for instance, a dehydration of a 1,8-dicarboxylic acid reaction intermediate using acetic anhydride. A synthesis of the lamellicolic anhydrides is also conceivable using acenaphthene, or one of its derivatives, as a starting material. In this approach, the anhydride moiety can be introduced by oxidation of the ethylene bridge. Prior to this oxidation, methyl, methoxy, and/or hydroxy functionalities may be introduced by different synthetic means available, including but not limited to, electrophilic and nucleophilic aromatic substitutions as described earlier. However, these reactions can also be completed after oxidation of the ethylene bridge to modulate aromatic directing effects, depending on the desired outcome of aromatic functionalisation reactions.

Biocatalysis or chemoenzymatic methodology may also be utilised to functionalise the aromatic positions of acenaphthene before synthesising the anhydride moiety by oxidation. These reaction steps can lead to lamellicolic anhydrides Ia-Ic or other derivatives in which the positions of the methyl, methoxy, and/or hydroxy functionalities are varied.

The properties of the adjuvant per se will be understood to provide the same advantages for an agrochemical formulation comprising said adjuvant. Therefore, an agrochemical formulation is provided, when comprising the adjuvant of the present invention, having the advantages of the properties of the adjuvant per se.

Agrochemically active compounds, including insecticides and fungicides, require a formulation which allows the active compounds to be taken up by the plant/the target organisms.

The term 'agrochemical formulation' as used herein refers to compositions including an active agrochemical, and is intended to include all forms of compositions, including concentrates and spray formulations. If not specifically stated, the agrochemical formulation of the present invention may be in the form of a concentrate, a diluted concentrate, or a sprayable formulation.

The adjuvant of the present invention may be combined with other components in order to form an agrochemical formulation comprising at least one agrochemical active.

Accordingly, agrochemical active compounds may be formulated as an emulsifiable concentrate (EC), emulsion concentrate (EW), suspension concentrate (SC), soluble liquid (SL), as an oil-based suspension concentrate (OD), and/or suspoemulsions (SE).

In an EC formulation and in an SL formulation, the active compound may be present in dissolved form, whereas in an OD, SC, EW, or SE formulations the active compound may be present as a solid or emulsified liquid.

It is envisaged that the adjuvant of the present invention will particularly find use in a EC, EW, SC, SL, OD, or SE formulation.

Agrochemical concentrates are agrochemical compositions, which may be aqueous or non-aqueous, and which are designed to be diluted with water (or a water-based liquid) to form the corresponding spray formulations. Said compositions include those in liquid form (such as solutions, emulsions, or dispersions) and in solid form (especially in water dispersible solid form) such as granules or powders.

Spray formulations are aqueous agrochemical formulations including all the components which it is desired to apply to the plants or their environment. Spray formulations can be made up by simple dilution of concentrates containing desired components (other than water), or by mixing of the individual components, or a combination of diluting a concentrate and adding further individual components or mixtures of components. Typically, such end use mixing is carried out in the tank from which the formulation is sprayed, or alternatively in a holding tank for filling the spray tank. Such mixing and mixtures are typically termed tank mixing and tank mixtures.

The adjuvant may therefore be incorporated into the formulation of the agrochemical active compound (in-can/built-in formulation) or be added after dilution of the concentrated formulation of the spray liquor (tank-mix). To avoid dosage errors and to improve user safety during application of agrochemical products, it is advantageous to incorporate the adjuvant into the formulation. This also avoids the unnecessary use of additional packaging material for the tank-mix products.

According to the needs of the customer, concentrates thus formed may comprise typically up to 95 wt. % agrochemical actives. Said concentrates may be diluted for use resulting in a dilute composition having an agrochemical active concentration of about 0.5 wt. % to about 1 wt. %. In said dilute composition (for example, a spray formulation, where a spray application rate may be from 10 to 500 $l \cdot ha^1$) the agrochemical active concentration may be in the range from about 0.001 wt. % to about 1 wt. % of the total formulation as sprayed.

The adjuvant of the present invention will typically be used in an amount proportional to the amount of the active agrochemical in the formulation. In agrochemical formulation concentrates, the proportion of the adjuvant will depend on the solubility of the components in the liquid carrier. Typically, the concentration of the adjuvant in such a concentrate will be from 1 wt. % to 99 wt. %. Preferably, the concentration of the adjuvant in such a concentrate will be from 1 wt. % to 70 wt. %. More preferably, the concentration of the adjuvant in such a concentrate will be from 3 wt. % to 50 wt. %.

Upon dilution to form, for example, a spray formulation, the adjuvant will typically be present at a concentration of from 0.01 wt. % to 2 wt. %, more usually from 0.03 wt. % to 0.5 wt. % of the spray formulation. Further preferably, the adjuvant will be present at a concentration of from 0.12 wt. % to 0.4 wt. % of the spray formulation.

The ratio of adjuvant to active agrochemical in the agrochemical formulation is preferably from about 1:40 to about 1:1. More preferably, the ratio of adjuvant to active agrochemical in the agrochemical formulation is from about 1:20 to about 1:1. Further preferably, the ratio of adjuvant to active agrochemical in the agrochemical formulation is from about 1:5 to 1 about 1:1. This ratio range will generally be maintained for concentrate forms of formulations (e.g. where the adjuvant is included in a dispersible liquid concentrate or dispersible solid granule formulation), and in the spray formulations.

When concentrates (solid or liquid) are used as the source of the active agrochemical and/or adjuvant, the concentrates will typically be diluted to form the spray formulations. The dilution may be with from 1 to 10,000, particularly 10 to 1,000, times the total weight of the concentrate of water to form the spray formulation.

Where the agrochemical active is present in the aqueous end use formulation as solid particles, most usually it will be present as particles mainly of active agrochemical. However, if desired, the active agrochemical can be supported on a solid carrier e.g. silica or diatomaceous earth, which can be a solid support, filler or diluent material as mentioned above.

The spray formulations will typically have a pH within the range from moderately acidic (e.g. about 3) to moderately alkaline (e.g. about 10), and particularly near neutral (e.g. about 5 to 8). More concentrated formulations will have similar degrees of acidity/alkalinity, but as they may be largely non-aqueous, pH is not necessarily an appropriate measure of this.

The agrochemical formulation may include solvents (other than water) such as monopropylene glycol, oils which can be vegetable or mineral oils such as spray oils (oils included in spray formulations as non-surfactant adjuvants), associated with the first and co-adjuvants. Such solvents may be included as a solvent for the adjuvant, and/or as a humectant, e.g. especially propylene glycol. When used, such solvents will typically be included in an amount of from 5 wt. % to 500 wt. %, desirably 10 wt. % to 100 wt. %, by weight of the adjuvant. Such combinations can also include salts such as ammonium chloride and/or sodium benzoate, and/or urea especially as gel inhibition aids.

In an alternative embodiment, either the adjuvants of the present invention, or the organism according to the sixth aspect may be included in a seed coating composition suitable for applying to seeds. Preferably, the adjuvants of the present invention may be included in the seed coating composition.

The adjuvants are suitably present in the seed coating composition at a concentration in the range from 0.5 to 25 wt. %, preferably 2 to 18 wt. %, more preferably 5 to 15 wt. %, in particular 8 to 12 wt. % based on the total weight of the composition.

The coating may include film coating, pelleting, and encrusting or a combination of these techniques as known in the art. It is envisaged that the present invention applies to all said coating types, preferably to film coating.

The seed coating composition of the invention may be applied to the seed in conventional manners.

The seed may be primed or not primed (having been subjected to a treatment to improve the germination rate, e.g. osmopriming, hydropriming, matrix priming).

In one embodiment, the seed is not provided with artificial layers prior to applying the seed coating composition of the invention, for example primer layers comprising a binder, such as a polymer. Accordingly, the seed coating composition is preferably applied directly on the natural outer surface of the seed. Nonetheless, it is possible that the seed surface has undergone a surface treatment prior to applying the seed coating composition.

Preferably, the seed coating composition is applied as a liquid composition and/or emulsion and/or dispersion and/or latex composition and thereafter solidified (including cured and/or dried) to form a seed coating. The term "liquid coating composition" as used in this application is meant to include coating compositions in the form of a suspension, emulsion, and/or dispersion, preferably a dispersion.

Conventional means of coating may be employed for coating the seeds. Various coating machines are available to the person skilled in the art. Some well-known techniques include the use of drum coaters, fluidised bed techniques, rotary coaters (with and without integrated drying), and spouted beds. Suitably, the seed coating composition is applied to the seed by a rotary coater, a rotary dry coater, a pan coater or a continuous treater.

The seed coating composition can, for instance, be applied by film coating, spraying, dipping, or brushing of the seed coating composition. Preferably, the method comprises applying the seed coating composition to form a film or seed coating layer. Seed coating typically involves forming on the surface of the seeds a firmly adhering, moisture permeable coating. The process typically comprises applying a liquid seed coating composition to the seeds before planting.

An additional film coat layer may optionally be applied over the top of the coating layer of the invention to provide additional benefits, including but not limited to cosmetics, coverage, actives, nutrients, and processing improvements such as faster drying, seed flow, durability and the like.

The agrochemical formulation or seed coating composition may also include other components as desired. These other components may be selected from those including:

binders, particularly binders which are readily water soluble to give low viscosity solutions at high binder concentrations, such as polyvinylpyrrolidone; polyvinyl alcohol; carboxymethyl cellulose; gum arabic; sugars e.g. sucrose or sorbitol; starch; ethylene-vinyl acetate copolymers, sucrose and alginates;

diluents, absorbents or carriers such as carbon black; talc; diatomaceous earth; kaolin; aluminium, calcium or magnesium stearate; sodium tripolyphosphate; sodium tetraborate; sodium sulphate; sodium, aluminium and mixed sodium-aluminium silicates; and sodium benzoate;

- disintegration agents, such as surfactants, materials that swell in water, for example carboxy methylcellulose, collodion, polyvinylpyrrolidone and microcrystalline cellulose swelling agents; salts such as sodium or potassium acetate, sodium carbonate, bicarbonate or sesquicarbonate, ammonium sulphate and dipotassium hydrogen phosphate;
- wetting agents such as alcohol ethoxylate and alcohol ethoxylate/propoxylate wetting agents;
- dispersants such as sulphonated naphthalene formaldehyde condensates and acrylic copolymers such as the comb copolymer having capped polyethylene glycol side chains on a polyacrylic backbone;
- emulsifiers such as alcohol ethoxylates, ABA block co polymers, or castor oil ethoxylates;
- antifoam agents, e.g. polysiloxane antifoam agents, typically in amounts of 0.005 wt. % to 10 wt. % of the formulation;
- viscosity modifiers such as commercially available water soluble or miscible gums, e.g. xanthan gums, and/or cellulosics, e.g. carboxy-methyl, ethyl or propylcellulose; and/or
- preservatives and/or anti-microbials such as organic acids, or their esters or salts such as ascorbic e.g. ascorbyl palmitate, sorbic e.g. potassium sorbate, benzoic e.g. benzoic acid and methyl and propyl 4-hydroxybenzoate, propionic e.g. sodium propionate, phenol e.g. sodium 2-phenylphenate; 1,2-benzisothiazolin-3-one; or formaldehyde as such or as paraformaldehyde; or inorganic materials such as *sulphurous* acid and its salts, typically in amounts of 0.01 wt. % to 1 wt. % of the formulation.

The agrochemical formulation or seed coating composition according to the present invention may also contain components, such as surfactant materials which form part of the emulsifier system. Said surfactants may include surfactant dispersants. Other adjuvants not within the scope of the present invention, such as surfactant adjuvants, may be included in the compositions and formulations of and used in this invention. Examples include alkylpolysaccharides (more properly called alkyl oligosaccharides); fatty amine ethoxylates e.g. coconut alkyl amine 2EO; and derivatives of alk(en)yl succinic anhydride, in particular those described in PCT applications WO 94/00508 and WO 96/16930.

The formulation/composition may comprise one or more biologically active ingredients (including plant enhancing agents, in particular plant protective products (also referred to as PPPs)). Suitable examples of active ingredients, in particular plant enhancing agents, are fungicidal agents, bactericidal agents, insecticidal agents, nematicidal agents, molluscicidal agents, biologicals, acaricides or miticides, pesticides, and biocides. Further possible active ingredients include disinfectants, microorganisms, rodent killers, weed killers (herbicides), attracting agents, (bird) repellent agents, plant growth regulators (such as gibberellic acid, auxin or cytokinin), nutrients (such a potassium nitrate, magnesium sulphate, iron chelate), plant hormones, minerals, plant extracts, germination stimulants, pheromones, biological preparations, etc.

Suitable agrochemical actives for use in the formulations or seed coating composition according to the invention are all agrochemically active compounds that may be solid or liquid at room temperature. It is envisaged that the adjuvant of the present invention would have broad applicability to all types of agrochemical actives.

Agrochemical actives refer to biocides which, in the context of the present invention, are plant protection agents, more particular chemical substances capable of killing different forms of living organisms used in fields such as medicine, agriculture, forestry, and mosquito control. Also counted under the group of biocides are so-called plant growth regulators.

Biocides for use in agrochemical formulations or seed coating compositions of the present invention are typically divided into two sub-groups:

- pesticides, including fungicides, herbicides, insecticides, algicides, molluscicides, miticides and rodenticides; and
- antimicrobials, including germicides, antibiotics, antibacterials, antivirals, antifungals, antiprotozoals and antiparasites.

In particular, biocides selected from insecticides, fungicides, or herbicides may be particularly preferred.

The term 'pesticide' will be understood to refer to any substance or mixture of substances intended for preventing, destroying, repelling, or mitigating any pest. A pesticide may be a chemical substance or biological agent (such as a virus or bacteria) used against pests including insects, plant pathogens, weeds, mollusks, birds, mammals, fish, nematodes (roundworms) and microbes that compete with humans for food, destroy property, spread disease or are a nuisance. In the following examples, pesticides suitable for the agrochemical compositions according to the present invention are given. A fungicide is a chemical control of fungi. Fungicides are chemical compounds used to prevent the spread of fungi in gardens and crops. Fungicides are also used to fight fungal infections. Fungicides can either be contact or systemic. A contact fungicide kills fungi when it comes into contact with the fungicide retained on leaf surfaces. A systemic fungicide is absorbed into plant tissues and kills the fungus when it attempts to invade the host.

Examples for suitable fungicides, according to the present invention, encompass the following species: (3-ethoxypropyl)mercury bromide, 2-methoxyethylmercury chloride, 2-phenylphenol, 8-hydroxyquinoline sulphate, 8-phenylmercuri oxyquinoline, acibenzolar, acylamino acid fungicides, acypetacs, aldimorph, aliphatic nitrogen fungicides, allyl alcohol, amide fungicides, ampropylfos, anilazine, anilide fungicides, antibiotic fungicides, aromatic fungicides, aureofungin, azaconazole, azithiram, azoxystrobin, barium polysulphide, benalaxyl-M, benodanil, benomyl, benquinox, bentaluron, benthiavalicarb, benzalkonium chloride, benzamacril, benzamide fungicides, benzamorf, benzanilide fungicides, benzimidazole fungicides, benzimidazole precursor fungicides, benzimidazolylcarbamate fungicides, benzohydroxamic acid, benzothiazole fungicides, bethoxazin, binapacryl, biphenyl, bitertanol, bithionol, blasticidin-S, Bordeaux mixture, boscalid, bridged diphenyl fungicides, bromuconazole, bupirimate, Burgundy mixture, buthiobate, butylamine, calcium polysulphide, captafol, captan, carbamate fungicides, carbamorph, carbanilate fungicides, carbendazim, carboxin, carpropamid, carvone, Cheshunt mixture, chinomethionat, chlobenthiazone, chloraniformethan, chloranil, chlorfenazole, chlorodinitronaphthalene, chloroneb, chloropicrin, chlorothalonil, chlorquinox, chlozolinate, ciclopirox, climbazole, clotrimazole, conazole fungicides, conazole fungicides (imidazoles), conazole fungicides (triazoles), copper(II) acetate, copper (II) carbonate, basic, copper fungicides, copper hydroxide, copper naphthenate, copper oleate, copper oxychloride, copper(II) sulphate, copper sulphate, basic, copper zinc chromate, cresol, cufraneb, cuprobam, cuprous oxide, cyazofamid, cyclafuramid, cyclic dithiocarbamate fungicides, cycloheximide, cyflufenamid, cymoxanil, cypendazole, cyproconazole, cyprodinil, dazomet, DBCP, debacarb, decafentin, dehydroacetic acid, dicarboximide fungicides, dichlofluanid, dichlone, dichlorophen, dichlorophenyl, dicarboximide fungicides, dichlozoline, diclobutrazol, diclocymet, diclomezine, dicloran, diethofencarb, diethyl pyrocarbonate, difenoconazole, diflumetorim, dimethirimol, dimethomorph, dimoxystrobin, diniconazole, dinitrophenol fungicides, dinobuton, dinocap, dinocton, dinopenton, dinosulphon, dinoterbon, diphenylamine, dipyrithione, disulphiram, ditalimfos, dithianon, dithiocarbamate fungicides, DNOC, dodemorph, dodicin, dodine, donatodine, drazoxolon, edifenphos, epoxiconazole, etaconazole, etem, ethaboxam, ethirimol, ethoxyquin, ethylmercury 2,3-dihydroxypropyl mercaptide, ethylmercury acetate, ethylmercury bromide, ethylmercury chloride, ethylmercury phosphate, etridiazole, famoxadone, fenamidone, fenaminosulph, fenapanil, fenarimol, fenbuconazole, fenfuram, fenhexamid, fenitropan, fenoxanil, fenpiclonil, fenpropidin, fenpropimorph, fentin, ferbam, ferimzone, fluazinam, fludioxonil, flumetover, fluopicolide, fluoroimide, fluotrimazole, fluoxastrobin, fluquinconazole, flusilazole, flusulphamide, flutolanil, flutriafol, folpet, formaldehyde, fosetyl, fuberidazole, furalaxyl, furametpyr, furamide fungicides, furanilide fungicides, furcarbanil, furconazole, furconazole-cis, furfural, furmecyclox, furophanate, glyodin, griseofulvin, guazatine, halacrinate, hexachlorobenzene, hexachlorobutadiene, hexachlorophene, hexaconazole, hexylthiofos, hydrargaphen, hymexazol, imazalil, imibenconazole, imidazole fungicides, iminoctadine, inorganic fungicides, inorganic mercury fungicides, iodomethane, ipconazole, iprobenfos, iprodione, iprovalicarb, isoprothiolane, isovaledione, kasugamycin, kresoxim-methyl, lime sulphur, mancopper, mancozeb, maneb, mebenil, mecarbinzid, mepanipyrim, mepronil, mercuric chloride, mercuric oxide, mercurous chloride, mercury fungicides, metalaxyl, metalaxyl-M, metam, metazoxolon, metconazole, methasulphocarb, methfuroxam, methyl bromide, methyl isothiocyanate, methylmercury benzoate, methylmercury dicyandiamide, methylmercury pentachlorophenoxide, metiram, metominostrobin, metrafenone, metsulphovax, milneb, morpholine fungicides, myclobutanil, myclozolin, N-(ethylmercury)-p-toluenesulphonanilide, nabam, natamycin, nitrostyrene, nitrothal-isopropyl, nuarimol, OCH, octhilinone, ofurace, organomercury fungicides, organophosphorus fungicides, organotin fungicides, orysastrobin, oxadixyl, oxathiin fungicides, oxazole fungicides, oxine copper, oxpoconazole, oxycarboxin, pefurazoate, penconazole, pencycuron, pentachlorophenol, penthiopyrad, phenylmercuriurea, phenylmercury acetate, phenylmercury chloride, phenylmercury derivative of pyrocatechol, phenylmercury nitrate, phenylmercury salicylate, phenylsulphamide fungicides, phosdiphen, phthalide, phthalimide fungicides, picoxystrobin, piperalin, polycarbamate, polymeric dithiocarbamate fungicides, polyoxins, polyoxorim, polysulphide fungicides, potassium azide, potassium polysulphide, potassium thiocyanate, probenazole, prochloraz, procymidone, propamocarb, propiconazole, propineb, proquinazid, prothiocarb, prothioconazole, pyracarbolid, pyraclostrobin, pyrazole fungicides, pyrazophos, pyridine fungicides, pyridinitril, pyrifenox, pyrimethanil, pyrimidine fungicides, pyroquilon, pyroxychlor, pyroxyfiir, pyrrole fungicides, quinacetol, quinazamid, quinconazole, quinoline fungicides, quinone fungicides, quinoxaline fungicides, quinoxyfen, quintozene, rabenzazole, salicylanilide, silthiofam, simeconazole, sodium azide, sodium orthophenylphenoxide, sodium pentachlorophenoxide, sodium polysulphide, spiroxamine, streptomycin, strobilurin fungicides, sulphonanilide fungicides, sulphur, sultropen, TCMTB, tebuconazole, tecloftalam, tecnazene, tecoram, tetraconazole, thiabendazole, thiadifluor, thiazole fungicides, thicyofen, thifluzamide, thiocarbamate fungicides, thiochlorfenphim, thiomersal, thiophanate, thiophanate-methyl, thiophene fungicides, thioquinox, thiram, tiadinil, tioxymid, tivedo, tolclofos-methyl, tolnaftate, tolylfluanid, tolylmercury acetate, triadimefon, triadimenol, triamiphos, triarimol, triazbutil, triazine fungicides, triazole fungicides, triazoxide, tributyltin oxide, trichlamide, tricyclazole, trifloxystrobin, triflumizole, triforine, triticonazole, unclassified fungicides, undecylenic acid, uniconazole, urea fungicides, validamycin, valinamide fungicides, vinclozolin, zarilamid, zinc naphthenate, zineb, ziram, zoxamide, and mixtures thereof.

A herbicide is a pesticide used to kill unwanted plants. Selective herbicides kill specific targets while leaving the desired crop relatively unharmed. Some of these act by interfering with the growth of the weed and are often based on plant hormones. Herbicides used to clear waste ground are non-selective and kill all plant material with which they come into contact. Herbicides are widely used in agriculture and in landscape turf management. They are applied in total vegetation control (TVC) programs for maintenance of highways and railroads. Smaller quantities are used in forestry, pasture systems, and management of areas set aside as wildlife habitat.

Suitable herbicides may be selected from the group comprising: aryloxycarboxylic acid e.g. MCPA, aryloxyphenoxypropionates e.g. clodinafop, cyclohexanedione oximes e.g. sethoxydim, hydroxybenzonitriles e.g. bromoxynil, sulphonylureas e.g. nicosulphuron, triazolopyrimidines e.g. penoxsulam, triketiones e.g. mesotriones, triazine herbicides such as metribuzin, hexaxinone, or atrazine; sulphonylurea herbicides such as chlorsulfuron; uracils such as lenacil, bromacil, or terbacil; urea herbicides such as linuron, diuron, siduron, or neburon; acetanilide herbicides such as alachlor, or metolachlor; thiocarbamate herbicides such as benthiocarb, triallate; oxadiazolone herbicides such as oxadiazon; isoxazolidone herbicides, phenoxyacetic acids; diphenyl ether herbicides such as fluazifop, acifluorfen, bifenox, or oxyfluorfen; dinitro aniline herbicides such as trifluralin; organophosphonate herbicides such as glufosinate salts and esters and glyphosate salts and esters; and/or dihalobenzonitrile herbicides such as bromoxynil, or ioxynil, benzoic acid herbicides, dipyridilium herbicides such as paraquat; and other herbicides such as clomazone, carfentrazone, saflufenacil, and pyroxasulphone.

Particularly preferred herbicides may be selected from 2,4-dichlorophenoxyacetic acid (2,4-D), atrazine, dicamba as benzoic acid, glyphosate, glufosinate, imazapic as imidazolinone, metolachlor as chloroacetamide, picloram, clopyralid, and triclopyr as pyridinecarboxylic acids or synthetic auxins, their respective water soluble salts and esters, and mixtures thereof.

An insecticide is a pesticide used against insects in all developmental forms, and include ovicides and larvicides used against the eggs and larvae of insects. Insecticides are used in agriculture, medicine, industry and the household.

Suitable insecticides may include those selected from: chlorinated insecticides such as, for example, Camphechlor, DDT, Hexachloro-cyclohexane, gamma-Hexachlorocyclohexane, Methoxychlor, Pentachlorophenol, TDE, Aldrin, Chlordane, Chlordecone, Dieldrin, Endosulphan, Endrin, Heptachlor, Mirex and their mixtures; organophosphorous compounds such as, for example, Acephate, Azinphos-methyl, Bensulide, Chlorethoxyfos, Chlorpyrifos, Chlorpyriphos-methyl, Diazinon, Dichlorvos (DDVP), Dicrotophos, Dimethoate, Disulphoton, Ethoprop, Fenamiphos, Fenitrothion, Fenthion, Fosthiazate, Malathion, Methamidophos, Methidathion, Methyl-parathion, Mevinphos, Naled, Omethoate, Oxydemeton-methyl, Parathion, Phorate, Phosalone, Phosmet, Phostebupirim, Pirimiphos-methyl, Profenofos, Terbufos, Tetrachlorvinphos, Tribufos, Trichlorfon and their mixture; carbamates such as, for example, Aldicarb, Carbofuran, Carbaryl, Methomyl, 2-(1-Methylpropyl) phenyl methylcarbamate and their mixtures; pyrethroids such as, for example, Allethrin, Bifenthrin, Deltamethrin, Permethrin, Resmethrin, Sumithrin, Tetramethrin, Tralomethrin, Transfluthrin and their mixtures; plant toxin derived compounds such as, for example, Derris (rotenone), Pyrethrum, Neem (Azadirachtin), Nicotine, Caffeine and their mixture; neonicotinoids such as imidacloprid; abamectin e.g. emamactin; oxadiazines such as indoxacarb; and/or anthranilic diamides such as rynaxypyr.

Miticides are pesticides that kill mites. Antibiotic miticides, carbamate miticides, formamidine miticides, mite growth regulators, organochlorine, permethrin and organophosphate miticides all belong to this category. Molluscicides are pesticides used to control mollusks, such as moths, slugs and snails. These substances include metaldehyde, methiocarb and aluminium sulphate. A nematicide is a type of chemical pesticide used to kill parasitic nematodes (a phylum of worm).

Most preferably, the active present in the agrochemical formulation or seed coating composition of the present invention is selected from triazoles fungicides, strobilurins fungicides, or a combination thereof. In particular, tebuconazole, flutriafol, carbendazim, azoxystrobin, kresoxim-methyl, cyproconazole, or pyraclostrobin.

Nutrients may be present in addition to, or as an alternative to, agrochemical actives. In such formulations/compositions the nutrient is typically in a dry form.

The nutrients may preferably be a solid phase nutrients. Solid nutrients are to be understood in the present invention as meaning substances whose melting point is above 20° C. (at standard pressure). Solid nutrients will also include insoluble nutrient ingredients, i.e. nutrient ingredients whose solubility in water is such that a significant solid content exists in the concentrate after addition.

Nutrients refer to chemical elements and compounds which are desired or necessary to promote or improve plant growth. Suitable nutrients generally are described as macronutrients or micronutrients. Suitable nutrients for use in the concentrates according to the invention are all nutrient compounds.

Micronutrients typically refer to trace metals or trace elements, and are often applied in lower doses. Suitable micronutrients include trace elements selected from zinc, boron, chlorine, copper, iron, molybdenum, and manganese. The micronutrients may be in a soluble form or included as insoluble solids, and may be salts or chelated.

Macronutrients typically refer to those comprising nitrogen, phosphorus, and potassium, and include fertilisers such as ammonium sulphate, and water conditioning agents. Suitable macro nutrients include fertilisers and other nitrogen, phosphorus, potassium, calcium, magnesium, sulphur containing compounds, and water conditioning agents.

Suitable fertilisers include inorganic fertilisers that provide nutrients such as nitrogen, phosphorus, potassium or sulphur. Fertilisers may be included in diluted formulations at relatively low concentrations or as more concentrated solutions, which at very high levels may include solid fertiliser as well as solution.

It is envisaged that inclusion of the nutrient would be dependent upon the specific nutrient, and that micronutrients would typically be included at lower concentrations whilst macronutrients would typically be included at higher concentrations.

Biostimulant component may be added to the formulation or seed coating composition to promote growth of a crop plant. The biostimulant component may comprise or consist of one or more biostimulants.

Examples of useful biostimulants include, but are not limited to, plant growth hormones and plant growth regulators, such as cytokinins, auxins, gibberellins, ethylene, abscisic acid. Other biostimulants include, protein hydrolysate derivatives, seaweed extracts, amino acids, botanical extracts, chitosan derivatives, biopolymers, inorganic compounds, humic substances, microbial inoculants and microbial products, or mixtures thereof.

The adjuvant of the present invention will provide adjuvancy to the agrochemical formulation in which it is comprised, and particular may find application providing fungicide adjuvancy.

As used herein, the term 'adjuvant' or 'adjuvancy' refers to compounds which when added to an agrochemical formulation will improve the agrochemical's desired effect. The adjuvant may affect the diluent, the mixture, the active, or the target by its improvements of the active's performance. An adjuvant can be used to adhere the pesticide on the area where the pesticide is functional, change the epidermal layer of the leaf surface permitting pesticide entry, and/or sensitise the target pest to the active pesticide in an agrochemical formulation.

Specific adjuvancy effects may include surfactants, emulsifiers (dispersants and suspending agents), oils, emulsifiable oils, compatibility agents, buffering and conditioning agents, defoaming agents, deposition agents, drift control agents, thickeners, spreaders (wetters), stickers (builders and extenders), plant penetrants, translocators, soil penetrants, stabilising agents (UV filters), and/or pest sensitisation to the active pesticide.

Preferably, the adjuvants of the present invention may find use as either the sole component or principal functioning agent in adjuvants formulated either for tank-added use, or formulated directly into pesticide concentrates.

As a measure of the adjuvant activity in relation to the activity of the fungicide alone (e.g. pyraclostrobin) to *Botrytis cinerea* a value of percent inhibition (adjuvant and fungicide) divided by percent inhibition (fungicide) can be defined, with higher values desired. A value of 1 would therefore represent equal activity of the adjuvant/fungicide combination to the fungicide alone, whereas a value above 1 would represent higher activity with the adjuvant/fungicide combination than the fungicide alone. The actives of the present invention may have a value greater than 1. Preferably, the actives of the present invention have a value greater than 1.5, most preferably greater than 2.

All of the features described herein may be combined with any of the above aspects, in any combination.

EXAMPLES

In order that the present invention may be more readily understood, reference will now be made, by way of example, to the following description.

It will be understood that all tests and physical properties listed have been determined at atmospheric pressure and room temperature (i.e. 20-25° C.), unless otherwise stated herein, or unless otherwise stated in the referenced test methods and procedures.

Formation & Extraction

Bioassay-guided fractionation of the culture extracts of the fungus *Cosmospora* sp. RKDO 1747 led to the isolation of lamellicolic anhydrides and ilicicollins. The isolate RKDO1747 was cultured on YM (yeast extract malt extract) agar and incubated for 14 days at 22° C. Eight colony explants (approximately 3 $mm^3$) were used to inoculate 15 mL of YM broth in a sterile 50 mL test tube and shaken at 200 RPM, 22° C. for 5 days to create a seed inoculum. The seed culture was used to inoculate sterilised rice fermentation medium (1% brown rice and 2.5% mL YNB broth (0.67% g YNB powder, 0.5% sucrose)) prepared in Erlenmeyer flasks.

Following 21 days at 22° C., fermentations were extracted with 1 volume of ethyl acetate and shaken for 60 minutes at 175 RPM. Extracts were clarified by filtering through Whatman #3 filter paper and the solvent was removed in vacuo prior to chemical purification.

RKDO1747 fermentation extracts were fractionated on a Silasep C18 flash cartridge (43 g C-18) using a gradient of 10% MeOH:90% $H_2O$ to 100% MeOH over 20 minutes on a Teledyne Nextgen 300$^+$ Combiflash. Fractions were analysed on a Thermo Scientific Accela UHPLC coupled with a Thermo Exactive electrospray mass spectrometer (ESI-MS) with a SEDEX 80LT ELSD and a Thermo photodiode array (PDA) detector. Fractions containing lamellicolic anhydrides or ilicicolins were purified using reversed-phase C-18 HPLC (Kinetex 5 μm C18 column, 10×250 mm) on a Waters HPLC system with an evaporative light scattering detector (Waters 2424) and mass spectrometer (Waters 3100). Initial purification of the lamellicolic anhydrides was carried out with an isocratic elution of 60% aqueous MeCN with a flow rate of 3 mL/min. Ilicicolin H was eluted with an isocratic elution of 80% aqueous MeCN.

The structures of the lamellicolic anhydrides and ilicicolin H were elucidated by combined mass spectrometry and NMR analysis. NMR spectra were recorded on a Bruker Avance III 400 MHz NMR spectrometer operating at 400 and 150 MHz for $^1H$ and $^{13}C$, respectively. Spectra were referenced to residual undeuterated solvent peaks.

NMR analysis of the metabolites corresponding to m/z 261.0396 $[M+H]^+$ and m/z 434.2327 $[M+H]^+$ matched with literature data and confirmed the structures as lamellicolic anhydride (Ia) and ilicicolin H (A) respectively. The remaining four metabolites (m/z 275.0553 (Ic), 277.0342 (Ib), 289.0707 (Id & Ie) and 305.0657 (If & Ig) $[M+H]^+$) corresponded to further substituted lamellicolic anhydrides containing additional hydroxy and/or methoxy substitutions.

Lamellicolic anhydride (Ia): $^1H$ NMR (MeOD, 400 MHz): δ2.78 (s, 3H), 6.35 (s, H), 6.78 (s, H) ppm; HRMS (ESI) m/z: calcd for $C_{13}H_8O_6$ $[M+H]^+$ 261.0394, found 261.0396.

Lamellicolic anhydride 277 (Ib): $^1H$ NMR (MeOD, 400 MHz): δ2.84 (s, 3H), 6.78 (s, H) ppm; HRMS (ESI) m/z: calcd for $C_{13}H_8O_7$ $[M+H]^+$ 277.0343, found 277.0342.

Lamellicolic anhydride 275 (Ic): $^1H$ NMR (MeOD, 400 MHz): δ2.67 (s, 3H), 3.96 (s, H), 6.35 (s, H), 6.62 (s, H) ppm; HRMS (ESI) m/z: calcd for $C_{14}H_{10}O_6$ $[M+H]^+$ 275.0550, found 275.0553.

Lamellicolic anhydride 289 (Id & Ie): $^1H$ NMR (MeOD, 400 MHz): δ2.96 (s, 3H), 3.82 (s, 3H), 3.90 (s, 3H), 6.79 (s, H), 6.34 (s, H) ppm; HRMS (ESI) m/z: calcd for $C_{15}H_{12}O_6$ $[M+H]^+$ 289.0707, found 289.0708.

Lamellicolic anhydride 305 (If & Ig): $^1H$ NMR (MeOD, 400 MHz): δ2.66 (s, 3H), 3.77 (s, 3H), 3.96 (s, 3H), 6.37 (s, H) ppm; m/z: calcd for $C_{15}H_{12}O_7$ $[M+H]^+$ 305.0656, found 305.0657.

Adjutancy Examples

The parameters 'percent inhibition' and 'fold change' will be understood to represent ad be calculated as follows;

Percent Inhibition—The percent inhibition will be understood to represent the amount the fungicide and/or adjuvant inhibits the visible growth of the microorganism after 48 hours incubation at 22° C. relative to vehicle treated controls. This is calculated using the following formula:

$$[(Ø_C-Ø_T)/Ø_C]\times100\%$$

where:

$Ø_C$=diameter of colony grown on agar supplemented with vehicle (i.e. vehicle treated control), and $Ø_T$==diameter of colony grown on agar supplemented with fungicide and/or adjuvant formulated in an appropriate vehicle (i.e. solvent such as water EtOH, MeOH, MeCN, DMSO).

Fold Change—The fold change is a measure of the adjuvant/fungicide combination in inhibiting a microorganism compared to the fungicide alone. This indicates how the adjuvant performs relative to the fungicide alone. This is calculated using the following formula:

$$INH_{AF}/INH_F$$

where:

$INH_{AF}$=percent inhibition of fungal growth when treated with fungicide and adjuvant, and $INH_F$=percent inhibition of fungal growth when treated with fungicide alone.

Examples—Adjuvancy with Pyraclostrobin

*Botrytis cinerea* (ATCC 90479) was cultured on potato dextrose agar (PDA) for 7 days with diurnal UV cycles (12 h UV light and 12 h dark). Spores were harvested in a buffered, sterile saline solution (0.9% saline water with 1% Tween 80) and counted using a haemocytometer. The spore suspension was adjusted to a final concentration of 8.5×$10^6$ spores/mL to create a standardised inoculum.

To prepare hyphal fragments for adjuvant testing, 8.5×$10^4$ spores were used to inoculate 10 mL of potato dextrose broth in a 150×25 mm tube. The tube was incubated at 220 RPM, 22° C. for 48 hours. To create hyphal fragments from the culture, the culture was transferred to a 50 mL plastic conical tube containing approximately 20 sterile 5 mm diameter glass beads and vortexed for 5 min. After vortexing the tube was allowed to stand for 5 min to allow large mycelial clumps to settle and then the top layer containing hyphal fragments was removed and used as inocula for growth inhibition assays.

Fungicides and adjuvants were dissolved in methanol and added to molten PDA (~50° C.) and then the agar was distributed in the wells of 12 well multiwell plates (1 mL/well). The plates were cooled to room temperature and 10 μL of hyphal inoculum was added to the centre of each well. The plates were incubated at 22° C. for 48 hours and then the colony diameter was measured using a digital caliper. The biological growth control consisted of hyphae and vehicle (0.07% methanol), the negative control was media and vehicle (0.07% methanol).

The results of the adjuvant actives of the invention are shown in Table 1. Adjuvant activity with pyraclostrobin against *B. cinerea* was observed for each of the compounds tested, most notably lamellicolic anhydride 289 (Id & Ie) and 305 (If & Ig) which showed a 7.59 and 6.10 fold increase in fungicidal activity compared to pyraclostrobin alone at 0.1 μg/mL. Lamellicolic anhydride 289 (Id & Ie), lamellicolic anhydride 305 (If & Ig) and ilicicolin H (A) did not demonstrate any inherent fungicidal activity on their own at any of the concentrations tested.

TABLE 1

Effect of adjuvants on fungicidal activity of pyraclostrobin (pyra)

| Adjuvant | Adjuvant Concentration (μg/mL) | Fold Change in Growth Inhibition Pyra 0.8 μg/mL | Pyra 0.4 μg/mL | Pyra 0.2 μg/mL | Pyra 0.1 μg/mL |
|---|---|---|---|---|---|
| None | 0 | 1.00 | 1.00 | 1.00 | 1.00 |
| Lam 289 | 6.25 | 1.50 | 1.82 | 3.89 | 7.59 |
| (Id & Ie) | 3.13 | 1.48 | 1.95 | 3.79 | 7.04 |
| | 1.56 | 1.39 | 1.77 | 3.58 | 5.80 |
| Lam 305 | 3.13 | 1.46 | 1.63 | 3.26 | 6.10 |
| (If & Ig) | 1.56 | 1.39 | 1.74 | 3.78 | 5.98 |
| | 0.78 | 1.30 | 1.56 | 3.33 | 5.25 |
| Ilicicolin | 6.25 | 0.96 | 1.26 | 1.88 | 3.62 |
| H (A) | 3.13 | 1.21 | 1.35 | 2.43 | 3.51 |
| | 1.56 | 1.04 | 1.36 | 1.93 | 3.32 |

The effect of the adjuvants on fungicidal activity is represented as fold increase in growth inhibition. A value of 1 indicates no increase in fungicidal activity. A value less than 1 indicates reduced fungicidal activity and a value greater than 1 indicates increased fungicidal activity.

Examples—Cytotoxicity

The cytotoxicity of lamellicolic anhydride and ilicicolin H was assessed in vitro against African green monkey Vero kidney cells (ATCC CCL-81). Cells were grown and maintained in 15 mL of Eagle's minimal essential medium (Sigma M5650) supplemented with 10% fetal bovine serum (VWR #CA95043-976), 100 μU penicillin and 0.1 mg/mL streptomycin in T75 $cm^2$ cell culture flasks. Cells were incubated for 24 hours at 37° C. in a humidified atmosphere of 5% $CO_2$. Culture medium was refreshed every 2-3 days and cells were not allowed to exceed 80% confluency.

At 80% confluency the cells were counted, diluted and plated into 96 well cell culture plates (VWR #29442-054) at a cell density of 10,000 cells per well in 90 μL of growth medium. The plates were incubated at 37° C. in a humidified atmosphere of 5% $CO_2$ for 24 hours to allow cells to adhere to the plate before treatment. After 24 hours, adjuvants were solubilised in DMSO, serially diluted and added to the wells at final concentrations ranging from 1 μg/mL to 128 μg/mL. DMSO was used as the vehicle at a final concentration of 1% in the wells.

The plates were incubated at 37° C. in a humidified atmosphere of 5% $CO_2$ for 24 hours after which alamarBlue (Invitrogen) was added to each well at 10% of the culture volume. Fluorescence was monitored using a Thermo Scientific Varioskan Flash plate reader at 560/12 excitation, 590 nm emission both at time zero and 4 hrs after alamarBlue addition. After subtracting the time zero emission 590 nm measurement from the final reading, the inferred percentage of cell viability relative to the vehicle control wells was calculated.

Lamellicolic anhydride 289 (Id & Ie), lamellicolic anhydride 305 (If & Ig), and ilicicolin H (A) did not exhibit any cytotoxicity against Vero cells at the highest concentration tested (128 mg/mL) indicating that the adjuvants are not toxic to mammalian cells at the concentration tested.

Examples—Adjuvancy with Other Fungicides for *B. cinerea*

To expand the functional characterisation of the lamellicolic anhydride adjuvant (Ia) was tested in combination with seven fungicides belonging to six different fungicide groups as classified by the Fungicide Resistance Action Committee (FRAC Code List 2018). The effect of adjuvant-fungicide combinations on fungicidal activity against *B. cinerea* are shown in Table 2.

TABLE 2

Effect of (Ia) on fungicidal activity of seven fungicides

| Fungicide (FRAC Fungicide Code†) | Fungicide Concentration (μg/mL) | Fold Change in Growth Inhibition Lam 261 (Ia) 2 μg/mL | Lam 261 (Ia) 1 μg/mL |
|---|---|---|---|
| Dimethomorph (40) | 0 | 1.00 | 1.00 |
| | 0.8 | 16.06 | 17.72 |
| | 0.4 | 31.0 | n.t. |
| Prothioconazole (3) | 0 | 1.00 | 1.00 |
| | 1.0 | 26.91 | 5.53 |
| Mancozeb (M3) | 0 | 1.00 | 1.00 |
| | 0.2 | 2.83 | 2.44 |
| | 0.1 | 3.06 | 1.89 |
| Metalaxyl (4) | 0 | 1.00 | 1.00 |
| | 1.6 | 32.46 | 27.22 |
| | 0.8 | 45.13 | 31.72 |
| Benomyl (1) | 0 | 1.00 | 1.00 |
| | 0.0015 | 20.43 | 16.45 |
| Tebuconazole (3) | 0 | 1.00 | 1.00 |
| | 0.00075 | 9.79 | 9.37 |
| | 0.00018 | 21.61 | 15.13 |
| Captan (M4) | 0 | 1.00 | 1.00 |
| | 0.04 | 30.95 | 27.32 |
| | 0.008 | 32.35 | 17.25 |

†Fungicide codes are based on the Fungicide Resistance Action Committee mode of action codes (FRAC Code List 2018).

Numbers indicate fold change improvement in fungal growth inhibition relative to the fungal test organisms treated with fungicide and adjuvant vehicle alone. n.t. indicates not tested.

Adjuvant (Ia) provided a 16 to 45-fold increase in the fungicidal activity against *B. cinerea* with six of the seven fungicides. The lowest effect was observed with mancozeb, although even in this case, a 1.9 to 3.1-fold increase in fungicidal effect was observed.

These results clearly demonstrate that lamellicolic anhydride adjuvant (Ia), provide an adjuvant effect that is applicable to a multitude of fungicides belonging to different chemical classes with different modes of action.

The improved control was not due to an additive fungicidal effect because the adjuvant alone did not inhibit the growth of *B. cinerea* as indicated by a fold change value of 1, which indicates no effect on fungal growth.

Examples—Adjuvancy with Other Fungicides for Other Fungus

To evaluate the biological spectrum of activity, lamellicolic anhydride adjuvant (Ta) was tested in combination with seven fungicides against six different fungal test organisms belonging to five different genera.

Prior to evaluating the adjuvant effect of (Ia), the minimum inhibitory concentration (MIC) for each fungicide against each test organism was determined by measuring growth on agar plates containing decreasing concentrations of fungicide.

Once the MIC was determined, adjuvant testing was performed with the concentration of (Ta) fixed at 4 μg/mL and each fungicide at a concentration which inhibited growth of the fungus by 10-20%.

Results are shown in Table 3.

TABLE 3

Adjuvant effect of 4 μg/mL of Ia on the fungicidal activity of seven fungicides against six fungal target organisms

| Fungicide (FRAC Fungicide Code†) | Fungicide Conc. (μg/mL) | FT1 | FT2 | FT3 | FT4 | FT5 | FT6 |
|---|---|---|---|---|---|---|---|
| Pyrimethanil | 0.02 | n.t. | n.t. | n.t. | 1.31 | n.t. | n.t. |
| (9) | 0.006 | n.t. | n.t. | n.t. | n.t. | n.t. | 1.67 |
| Mancozeb | 0.2 | n.t. | n.t. | n.t. | 1.63 | 2.01 | n.t. |
| (M3) | 0.1 | n.t. | n.t. | 2.45 | n.t. | n.t. | n.t. |
| Dimethomorph | 12.8 | 1.63 | n.t. | n.t. | n.t. | 1.27 | n.t |
| (40) | 0.8 | n.t. | n.t. | n.t. | 1.85 | n.t. | n.t |
| | 0.2 | n.t. | n.t. | 1.25 | n.t. | n.t. | n.t. |
| Prothioconazole | 0.012 | n.t. | n.t. | n.t. | n.t. | 1.28 | n.t. |
| (3) | 0.006 | n.t. | n.t. | 1.50 | n.t. | n.t. | n.t. |
| | 0.00375 | n.t. | n.t. | n.t. | 1.52 | n.t. | n.t. |
| Iprodione (2) | 0.0015 | n.t. | n.t. | n.t. | 1.65 | 1.72 | n.t. |
| Pyraclostrobin | 0.01 | n.t. | 1.63 | n.t. | n.t. | n.t. | n.t. |
| (11) | 0.001 | n.t. | n.t. | 1.18 | 1.27 | n.t. | n.t. |
| Captan (M4) | 0.04 | n.t. | n.t. | n.t. | 1.17 | n.t. | n.t. |

†Fungicide codes are based on the Fungicide Resistance Action Committee mode of action codes (FRAC Code List 2018).

Fungal targets are: FT1 —*Fusarium solani*, FT2 —*Fusarium oxysporum*, FT3 —*Alternaria infectorium*, FT4 —*Penicillium roqueforti*, FT5 —*Aspergillus flavus*, FT6 —*Cladosporium* sp.

The numbers indicate fold change improvement in fungal growth inhibition relative to the fungal test organisms treated with fungicide and adjuvant vehicle alone. A value of 1 would indicate no effect on fungicidal activity, whilst a value >1 indicates improved fungicidal activity. n.t. indicates not tested.

Adjuvant activity was observed with dimethomorph against *Fusarium solani* (1.63-fold increase), with pyraclostrobin against *Fusarium oxysporum* (1.63-fold increase), with mancozeb, dimethomorph, prothioconazole and pyraclostrobin against *Alternaria infectorium* (2.45-, 1.25-, 1.50-, 1.18-fold increases, respectively), with pyrimethanil, mancozeb, dimethomorph, prothioconazole, iprodione, pyraclostrobin and captan against *P. roqueforti* (1.31-, 1.63-, 1.85-, 1.52-, 1.65-, 1.27-, 1.17-fold increases, respectively), with mancozeb, dimethomorph, prothioconazole and iprodione against *A. flavus* (2.01, 1.27, 1.28, 1.72-fold increases, respectively), and with pyrimethanil against *Cladosporium* sp. (1.67-fold increase).

These results demonstrate that the lamellicolic anhydride adjuvant (Ia) can improve the control of several fungal species in combination with multiple fungicides with different chemical structures and modes of action, thus further broadening the practical applications of the adjuvants described herein.

Examples—Phytotoxicity

Plant safety is a key characteristic of a fungicide adjuvant as the application of an adjuvant should not adversely affect plant health. To determine the safe use levels for lamellicolic anhydrides, phytotoxicity testing was performed on soybean (*Glycine max*, cv Alexa).

Soybean plants were grown by sowing single seeds inoculated with *Bradyrhizobium japonicum* (Novozymes GlyciMax) in Levington's M3 compost in 9 cm×9 cm plastic pots. The glasshouse temperatures were set to maintain 22° C.±2 during the day and 19° C.±2 during the night. The photoperiod was set to 14 h days.

Soybean plants were given supplementary lighting from SON-T bulbs. Biological control was used to prevent thrip damage (Bioline—*Amblyseius cucumeris*).

All plants were maintained at a well-watered status. Adjuvant treatments were applied to soybean plants once they reached the V4 stage (6 weeks). To retain treatments on leaf surfaces immediately after application, leaves were rested on platforms created from pot racks. The frames were stacked up high enough to allow the leaves to be laid out flat on top. Laminated sheets of card were taped onto the top of the frames to create a support for the leaves.

For the soybean plants, the central lobe of one fully expanded trifoliate leaf was held flat by taping down the edges carefully with Micropore tape.

Phytotoxicity was evaluated for two preparations, a crude fermentation extract containing ilicicolin and lamellicolic anhydrides prepared by extracting a solid rice fermentation with ethyl acetate, as well as a purified fraction containing lamellicolic anhydride 305 (If & Ig). These materials were prepared as described above.

The test materials were dissolved in 20% (v/v) DMSO at a concentration of 10 mg/mL and then a dilution series was prepared between 0.05-1 g/L while maintaining a 2% (v/v) DMSO concentration.

The positive phytotoxicity control was Synperonic A11 (1 g/L; obtainable from Croda), while the negative control was Atplus UEP-100 (1 g/L; obtainable from Croda).

The treatments were randomly allocated to a leaf site and marked using a fine-tip marker pen. For any given dilution rate, all treatments were able to fit on a single leaf A total of 8 replicate leaves on separate plants were used for each treatment dilution. Treatments were applied to the leaves as 10 μL drops. The lights above the plants were switched off during treatment application and were not switched back on until the droplets had dried fully.

Phytotoxicity was scored, and plants were assessed for phytotoxic tissue damage at 1 Day After Treatment (DAT), 7 and 14 DAT.

Results are shown in Table 4.

TABLE 4

Phytotoxicity assessment against soybean (Glycine max, cv Alexa).

| Sample | Concentration (g/L) | Phytotoxicity Score 1 DAT | 7 DAT | 14 DAT |
|---|---|---|---|---|
| Crude extract | 0.25 | 0.13 | 0.25 | 0.25 |
| | 0.1 | 0 | 0 | 0 |
| | 0.05 | 0 | 0 | 0 |
| | 0.025 | 0 | 0 | 0 |
| Lamellicolic anhydride 305 (If & Ig) | 0.25 | 0.25 | 0.38 | 0.38 |
| | 0.1 | 0.13 | 0.38 | 0.38 |
| | 0.05 | 0 | 0 | 0 |
| | 0.025 | 0 | 0 | 0 |
| Synperonic A11 | 1 | 2.04 | 2.30 | 2.30 |
| Atplus UEP-100 | 1 | 0 | 0.08 | 0.30 |

Phytotoxicity scale of 0 to 3 where:

0—no damage/necrosis; 1—slight spot-like necrosis on the area wetted by the drop; 2—ring-shaped necrosis; and 3—extended necrosis.

The observed phytotoxicity for crude extract and the lamellicolic anhydride 305 was below 0.4 when tested up to 0.25 mg/L per spot. This indicates that the phytotoxic effect was slight and limited to the spot wetted by the drop. At 0.1 mg/mL and below, no phytotoxic effect was observed for either of the test samples. As expected, Atplus UEP-100 showed only slight phytotoxic effects which only developed 14 DAT.

These results demonstrate that application of the adjuvant preparations prepared from *Cosmospora* sp. RKDO 1747 do not damage soybean tissues when applied at concentrations below 0.25 g/L and have no phytotoxic effects when applied at 0.1 or 0.05 g/L for the crude extract and lamellicolic anhydride 305 sample, respectively. As the adjuvant activity of the lamellicolic anhydrides is generally obtainable at concentrations below 0.01 g/L the rates required to obtain adjuvant activity are well below those at which phytotoxic effects are observed. It is to be understood that the invention is not to be limited to the details of the above embodiments, which are described by way of example only. Many variations are possible.

The invention claimed is:

1. An agrochemical formulation comprising:

i) an adjuvant that is a lamellicolic anhydride according to formula (I)

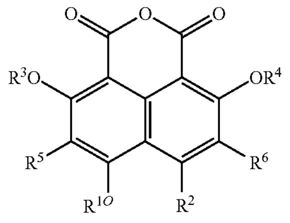

wherein:

$R^1$ is independently hydrogen or $C_1$ to $C_4$ alkyl;

$R^2$ is independently hydrogen, ethyl, n-propyl, isopropyl, n-butyl, isobutyl, sec-butyl, tert-butyl, hydroxyl, or $C_1$ to $C_4$ alkyoxyl;

$R^3$ and $R^4$ are independently hydrogen or $C_1$ to $C_4$ alkyl; and $R^5$ and $R^6$ are independently hydrogen, $C_1$ to $C_4$ alkyl, hydroxyl, or $C_1$ to $C_4$ alkyoxyl; and ii) at least one agrochemical active.

2. A concentrate formulation suitable for making the agrochemical formulation in accordance with claim 1, the concentrate comprising:

i) an adjuvant that is a lamellicolic anhydride according to formula (I)

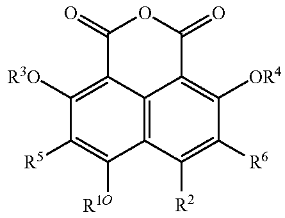

wherein:

$R^1$ is independently hydrogen or $C_1$ to $C_4$ alkyl;

$R^2$ is independently hydrogen, ethyl, n-propyl, isopropyl, n-butyl, isobutyl, sec-butyl, tert-butyl, hydroxyl, or $C_1$ to $C_4$ alkyoxyl;

$R^3$ and $R^4$ are independently hydrogen or $C_1$ to $C_4$ alkyl; and $R^5$ and $R^6$ are independently hydrogen, $C_1$ to $C_4$ alkyl, hydroxyl, or $C_1$ to $C_4$ alkyoxyl; and ii) at least one agrochemical active.

3. A method of treating vegetation to control pests, the method comprising applying the agrochemical formulation in accordance with claim 1, either to the vegetation or to the immediate environment of the vegetation.

4. An agrochemical formulation comprising:

i) an adjuvant that is a lamellicolic anhydride according to formula (I)

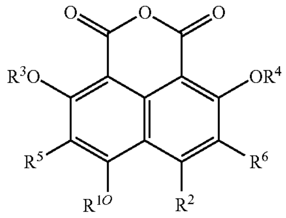

wherein:

$R^1$ is independently $C_1$ to $C_4$ alkyl;

$R^2$ is independently hydrogen, $C_1$ to $C_4$ alkyl or $C_1$ to $C_4$ alkyoxyl;

$R^3$ and $R^4$ are independently hydrogen or $C_1$ to $C_4$ alkyl; and $R^5$ and $R^6$ are independently hydrogen, $C_1$ to $C_4$ alkyl, hydroxyl, or $C_1$ to $C_4$ alkyoxyl; and ii) at least one agrochemical active.

5. The formulation according to claim 4, wherein compounds of formula (I) are selected from those where:

$R^1$ is methyl;

$R^2$ is independently hydrogen or methyl;

$R^3$ and $R^4$ are independently hydrogen or methyl; and $R^5$ and $R^6$ are independently hydrogen or hydroxyl.

6. A concentrate formulation suitable for making the agrochemical formulation in accordance with claim 4, the concentrate comprising:

i) an adjuvant that is a lamellicolic anhydride according to formula (I):

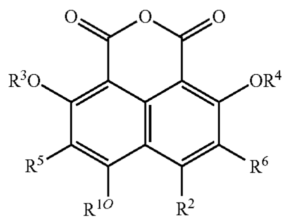

wherein:

$R^1$ is independently $C_1$ to $C_4$ alkyl;

$R^2$ is independently hydrogen, $C_1$ to $C_4$ alkyl or $C_1$ to $C_4$ alkyoxyl;

$R^3$ and $R^4$ are independently hydrogen or $C_1$ to $C_4$ alkyl; and $R^5$ and $R^6$ are independently hydrogen, $C_1$ to $C_4$ alkyl, hydroxyl, or $C_1$ to $C_4$ alkyoxyl; and ii) at least one agrochemical active.

7. A method of treating vegetation to control pests, the method comprising applying the agrochemical formulation in accordance with claim 4, either to the vegetation or to the immediate environment of the vegetation.

8. An agrochemical formulation comprising:

i) an adjuvant that is a lamellicolic anhydride selected from the following:

(Ib)

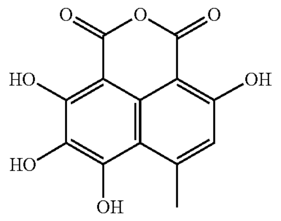

(Ic)

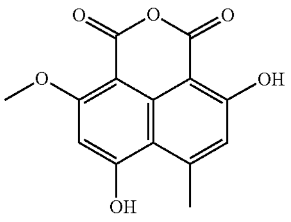

(Id)

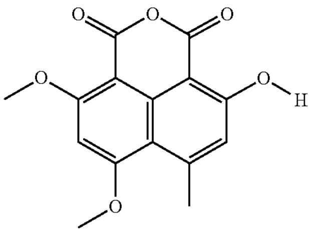

(Ie)

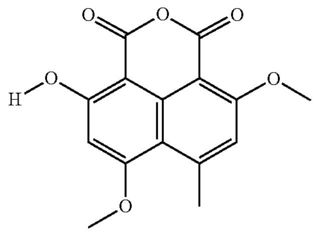

-continued (If)

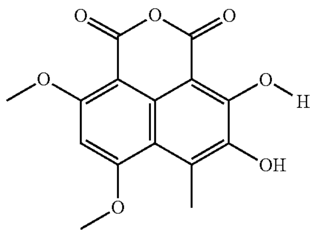

(Ig)

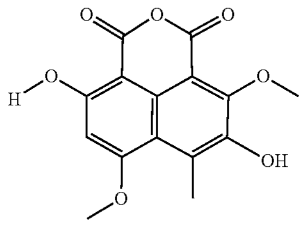

and ii) at least one agrochemical active.

9. A lamellicolic anhydride according to formula (I):

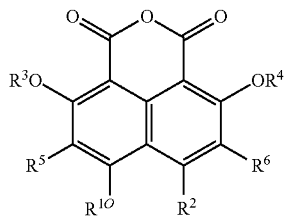

wherein:

$R^1$, $R^3$, $R^4$, and $R^6$ are hydrogen, $R^5$ is hydroxyl, and $R^2$ is methyl; or $R^1$, $R^4$, $R^5$, and $R^6$ are hydrogen, and $R^2$ and $R^3$ are methyl; or $R^4$, $R^5$, and $R^6$ are hydrogen, and $R^2$, $R^3$ and $R^1$ are methyl; or $R^3$, $R^5$, and $R^6$ are hydrogen, and $R^2$, $R^4$ and $R^1$ are methyl; or $R^4$ and $R^5$ are hydrogen, $R^2$, $R^3$ and $R^1$ are methyl, and $R^6$ is hydroxyl; or $R^3$ and $R^5$ are hydrogen, $R^2$, $R^4$ and $R^1$ are methyl, and $R^6$ is hydroxyl.

10. A seed coating composition comprising the lamellicolic anhydride in accordance with claim 9.

11. A lamellicolic anhydride according to formula (I):

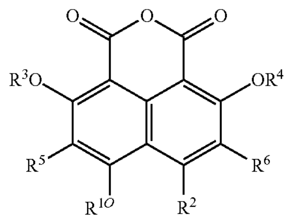

wherein:

$R^1$ is independently $C_1$ to $C_4$ alkyl;

$R^2$ is independently hydrogen, ethyl, n-propyl, isopropyl, n-butyl, isobutyl, sec-butyl, tert-butyl or $C_1$ to $C_4$ alkyoxyl;

$R^3$ and $R^4$ are independently hydrogen or $C_1$ to $C_4$ alkyl; and $R^5$ and $R^6$ are independently hydrogen, $C_1$ to $C_4$ alkyl, hydroxyl, or $C_1$ to $C_4$ alkyoxyl.

12. A seed coating composition comprising the lamellicolic anhydride in accordance with claim 11.

* * * * *